(12) United States Patent
Thompson et al.

(10) Patent No.: US 7,060,102 B2
(45) Date of Patent: Jun. 13, 2006

(54) FEMORAL IMPLANT FOR HIP ARTHROPLASTY

(76) Inventors: Matthew T. Thompson, 1820 Binz, #5, Houston, TX (US) 77004; James D. Johnson, 607 Kipling St., Apt. B, Houston, TX (US) 77006

( * ) Notice: Subject to any disclaimer, the term of this patent is extended or adjusted under 35 U.S.C. 154(b) by 0 days.

(21) Appl. No.: 10/762,213

(22) Filed: Jan. 21, 2004

(65) Prior Publication Data

US 2005/0159821 A1 Jul. 21, 2005

(51) Int. Cl.
*A61F 2/36* (2006.01)
(52) U.S. Cl. .................................... 623/23.35
(58) Field of Classification Search ............. 623/23.35, 623/23.15, 23.11, 23.19, 23.24, 23.31, 23.29, 623/23.3, 23.18
See application file for complete search history.

(56) References Cited

U.S. PATENT DOCUMENTS

| 4,957,510 | A |   | 9/1990 | Cremascoli |           |
|-----------|---|---|--------|------------|-----------|
| 5,358,534 | A | * | 10/1994| Dudasik et al. | 623/23.35 |
| 6,102,957 | A | * | 8/2000 | Noble et al. | 623/23.35 |
| 6,200,350 | B1| * | 3/2001 | Masini | 623/23.15 |
| 6,361,566 | B1|   | 3/2002 | Al-Hafez |  |
| 6,436,147 | B1| * | 8/2002 | Zweymuller | 623/22.41 |
| 6,723,130 | B1| * | 4/2004 | Draenert et al. | 623/23.35 |

OTHER PUBLICATIONS

"Improving Range of Motion & Minimizing Dislocation Through Innovative Design" Product Brochure, Wright Medical Technology (2002).

Nikou, C., et al., "Improved Range of Motion in THR by Reducing the Femoral Neck A/P Dimension," 45th Annual Meeting, Orthopedic Research Society, Anaheim, CA, p. 927 (Feb. 1999).
"Hip Prosthesis Cemented," Versys Hip System, Zimmer Product Brochure (1999).
"Competitive Comparison—Profemur Z—Total Hip System," Wright Medical Technology Product Brochure (2003).
"OMNIFIT EON—Decades of performance and clinical success," www.howost.com/primaryhip/cemented/eon.php (printed Nov. 5, 2003).
Vatani, N., et al., "Faulty Design Increases the Risk of Neck Fracture in a Hip Prosthesis," *Acta Orthop. Scand* 72(5):513-517 (2002).
"TMZF Alloy: A Titanium Alloy Optimized for Orthopedice Implants," Stryker Product Brochure (2002).
"AcuMatch Integrated Hip System," Exactech Product Brochure (1999).
Burstein, A.H., et al. "Neck Fractures of Femoral Prosthesis," *J. Bone and Joint Surgery*, 67-A(3): 497-499 (Mar. 1985).
Rand, J.A. and Chao, E.Y., "Femoral Implant Neck Fracture Following Total Hip Arthroplasty," *Clinical Orthopedics and Related Research*, 221: 255-259 (Aug. 1987).

(Continued)

*Primary Examiner*—Pedro Philogene
(74) *Attorney, Agent, or Firm*—Laura G. Barrow

(57) ABSTRACT

Novel femoral implants for use in hip arthroplasty are described and illustrated. The femoral implant comprise a stem and neck portion, with the neck portion having a novel configuration that provides for improved range in motion for the prosthesis without compromising strength of the implant.

42 Claims, 9 Drawing Sheets

OTHER PUBLICATIONS

Barrack, R.L., et al., "The Effect of Component Design on Range of Motion to Impingement in Total Hip Arthroplasty," *AAOS Instructional Course Lectures*, vol. 50, p. 275-280 (2001).

Barrack, R.L., et al. "Stem Design and Dislocation after Revision Total Hip Arthroplasty," *J. Arthroplasty* 16(8): 8-12 (2001) (suppl. 1).

Lee, E.W., and Kim, H.T., Early Fatigue Failures of Cemented, Forged, Cobalt-Chromium Femoral Stems of the Neck-Shoulder Junction, *J. Arthroplasty*, 16(2): 236-238 (2001).

Artime, V., Et al. "Fracture of the Neck of a Femoral Component in a Total Hip Arthroplasty: A Case Report," *Int. Orthopaedics (SICOT):*, 21:56-58 (1997).

"The Foundation Total Hip System" Encore Orthopedics Product Brochure (1997).

"Balance Hip Prosthesis—Primary Hip Surgical Technique," Biomet Product Brochure (1997).

PCT International Search Report for co-pending application PCT/US05/01822, based upon U.S. Appl. No. 10/762,213 (7 pages; Jul. 29, 2005).

* cited by examiner

FEMORAL IMPLANT FOR HIP ARTHROPLASTY

BACKGROUND AND SUMMARY OF THE INVENTION

Hip prostheses are designed to restore the normal motion and stability of the hip joint when disease prevents the original, native joint from functioning without pain or functional limitation. Typically the artificial joint comprises the following:

1. A femoral component, typically fabricated from a high-strength metal alloy (e.g. cobalt-chromium, titanium-aluminum-vanadium or stainless-steel). Most commonly, the femoral component consists of: (i) a highly polished metal ball (termed the femoral head of the prosthesis), which is designed to articulate against a mating socket, and (ii) an elongated stem that is inserted into the intramedullary shaft of the femur where it is fixed to the bone to stabilize the femoral head during loading. The head of the prosthesis is mounted on a tapered spigot which is attached to an elongated stem via an angled segment termed the "neck" of the prosthesis. The neck lies outside the confines of the bony canal in which the stem is anchored and occupies the space between the pelvis and the femur.

2. A hemispherical socket, commonly referred to as an "acetabular cup." This component is designed to articulate with the head of the femoral prosthesis. Acetabular cups are fabricated from a variety of materials, most commonly ultra high molecular weight (UHMW) polyethylene. Many designs consist of two elements: (i) a liner of wear-resistant polymeric or ceramic material, and (ii) a supporting metal shell, adapted for rigid fixation to the prepared surface of the acetabulum of the native pelvis.

Although it is intended that the prosthetic device will act like a normal joint in fully restoring the patient's range of motion and ease of movement, this goal is rarely achieved in practice. Most artificial hip prostheses allow the patient sufficient motion to perform many basic activities such as walking and sitting, but will not allow the patient to place his leg in more extreme positions accommodated by the normal joint. Although this is not a significant limitation when simple motions are involved (e.g. bending over and touching toes, or placing the thigh in contact with the chest), in many common activities of daily living, compound motions are involved. These motions require the femur to rotate about the hip joint in a plane that is not parallel or perpendicular to the front of the body. Common activities that necessitate compound rotations include rising from a low chair and picking up objects from the floor when seated. Other activities, such as crossing of the legs in a seated position or rolling over in bed, necessitate significant internal or external rotation of the femur about its longitudinal axis. In each of these situations, artificial hip joints typically allow significantly less motion than the normal joint, and attempts by the patient to force his hip to perform the activity will often cause dislocation of the joint, whereby the head of the femoral component is levered out of the acetabular cup. In most cases, the dislocated femoral head migrates to a position posterior to the pelvis with considerable pain and shortening of the limb.

The prevalence of dislocation after joint replacement is highly variable and is experienced by 0.7% to 5.5% of all patients after this surgical procedure. In patients who have to undergo implantation of a second artificial hip, the rate of dislocation is even greater, averaging between 5% and 20%.

The occurrence of dislocation is influenced by many variables, including the presence of additional disease processes, the laxity of the soft-tissue structures that surround the hip joint, and the alignment of the prosthetic components with respect to the femur and the pelvis. In the vast majority of cases, loss of stable articulation is preceded by a series of mechanical events that occur when the artificial joint is moved to the extremes of its arc of stable motion. During normal motion, the artificial hip approximates the motion of a ball-and-socket joint, with the femur moving about a point approximated by the center of rotation of the femoral head. If the femur is moved far enough from its initial, neutral position, mechanical contact or impingement will occur between either: a) the neck of the femoral stem and the edge of the bearing surface of the acetabular insert (referred to as "prosthetic impingement"), or b) points on the surface of the femur and the pelvis (referred to as "bony impingement").

Prosthetic impingement is the most frequent source of mechanical limitation to the artificial hip at the extremes of its range of motion. Once this occurs, additional motion of the lower limb is only possible if the femur and the femoral component pivot about the point of impingement between the neck of the prosthesis, which is most frequently located at the junction between the anterior edge of the concave bearing surface and the outer face of the component. This pivoting motion causes the head of the prosthesis to lift out of its mating recess in the acetabular insert. Once more than half of the head is raised above the contact point between the head and the bearing surface, the resistance to dislodgement of the head from the socket is too low to resist the forces acting on the joint, thereby resulting in dislocation. The most common activities leading to neck impingement and hip dislocation are stooping, rising from a chair, pivoting on one leg, rolling over while lying in bed, and leg-crossing. In the majority of these positions, impingement occurs on the anterior/medial side of the neck. A chain of events similar to those observed after prosthetic impingement also accompanies joint motion after bony impingement; however, in this case the pivot point for raising the femoral head is the point of contact between the pelvis and the femur.

Previous inventors have recognized the importance of preventing or delaying impingement as much as possible to afford the maximum possible motion to the hip joint without the onset of subluxation and instability. Several different design modifications to the neck of the prosthesis and the acetabular insert have been proposed to increase the allowable range of motion of the artificial joint prior to impingement. Currently, modifications to the neck have concentrated on two primary strategies: 1) maximizing the ratio between the diameter of the femoral head and the diameter of the neck; and 2) modifications to the cross-sectional shape of the neck to provide more motion in positions where impingement is predicted to occur during activities that commonly associated with dislocation. It is well recognized in the art that impingement between the femoral neck and the acetabular insert commonly occurs at points located between about 10 and 20 mm below the head center along the neck axis. The exact location of contact varies with the femoral head diameter and the design of the acetabular cup. It is also recognized that the range of motion of the hip to impingement increases dramatically with increasing head diameter and decreasing neck diameter; however, the choice of head diameter is generally limited by the minimum thickness of the acetabular liner, which must generally exceed 5 mm to provide adequate wear resistance. Further, it is recognized that the range of motion of hip prostheses is greatly influenced by variations in the position of the femoral and acetabular components with respect to the skeleton. In practice, it is necessary to anticipate a range of these positions to ensure that any one design will be effective in reducing the incidence of dislocation in clinical practice.

It is generally recognized that attempts to improve the range of motion of the artificial joint by narrowing the neck of the prosthesis are inherently limited by the minimum strength needed to avoid mechanical failure of the device during service within the body. In practice, the neck of the prosthesis is designed to withstand a minimum repetitive load applied to the head of the implant. Most implants are designed with necks that will resist 1,200–1,700 pounds of loading for 10 million cycles, depending upon the weight and activity level of the intended patient population. For necks that are circular in cross-section, this requirement necessitates that the neck have a diameter of at least 9 mm at the level along the axis of the neck where prosthetic impingement normally occurs. The precise value of neck diameter that is required to provide sufficient strength to avoid mechanical failure during the service life of the prosthetic device is a function of many factors, most notably the fatigue strength of the alloy utilized to fabricate the prosthesis and the severity, direction, and duration of loads applied to the device.

Though most femoral prostheses have necks that are circular in transverse cross-section, those skilled in the art have developed necks with non-circular necks to enhance the balance between strength and the motion of the joint. Consequently, prostheses exist that have necks with transverse cross-sections that are either circular 50, rectangular 52, oval 51, or trapezoidal 54 (FIG. 4). Although these strategies do increase the range of motion of the joint, they also lead to a significant reduction in strength, particularly when the load applied to the head of the prosthesis has a substantial anterior-posterior component which occurs during several strenuous activities, such as walking up and down stairs or rising from a chair. The magnitude of the anterior/posterior bending moment severely limits the extent to which the anterior-posterior width of the neck may be reduced to improve motion and is a fundamental deficiency of some early trapezoidal designs. Consequently, modifications to the neck to increase range of motion must be offset by increasing all dimensions of the part to regain strength. This partly reduces the gains in motion derived from the original change in cross-sectional shape.

The present invention is directed to a femoral implant for use in hip arthroplasty whereby the neck portion is designed to provide an improved balance between the range of motion of the joint during common activities and the resistance of the device to mechanical failure through its neck portion. These benefits will be realized independent of the strength of the resulting neck; however, the absolute values of neck strength will naturally increase if the dimensions of the neck are increased, with concomitant reduction in joint motion. Conversely, reductions in the dimensions of the neck, while maintaining the transverse shape taught by the invention, will lead to increased absolute motion in combination with reduced mechanical strength. Specifically, the implant comprises a longitudinal stem having a distal end and a proximal end, the stem further having a longitudinal axis extending from the proximal end to the distal end. The implant includes a neck portion extending from the proximal end of the stem and a femoral head configured for engagement within an acetabulum. The neck portion further has an axis extending through the femoral head and neck portion and intersecting the stem axis. A transverse cross section of the neck portion, taken perpendicular to the neck axis, further comprises: (i) a medial/lateral axis bisecting the cross-section through a medial-most point along the medial edge and the lateral-most point along the lateral edge of the cross-section, thereby creating two anterior and posterior halves about the medial/lateral axis, further defining a maximum medial/lateral width of the cross-section; and (ii) an anterior/posterior axis, perpendicularly intersecting the medial/lateral axis. The transverse cross-section further has a configuration defined by a medially-positioned circle comprising: (i) the medial-most point of the cross section, (ii) a point taken along the anterior edge of the cross section, and (iii) a point taken along the posterior edge of the cross section, wherein each of the anterior and posterior edge points are located along the anterior and posterior edges, respectively, at a distance of 10% of the medial/lateral width measured laterally from the medial-most edge point. The medially-positioned circle further has a medial diameter ranging in length of about 66% or less of the maximum anterior/posterior width of the cross section. More preferably, the medial diameter of the circle is about 45–55%, most preferably about 50% of the maximum anterior/posterior width of the cross section. Finally, the transverse cross section may be taken at any point located at or between about 10 mm to about 22 mm below the center of the femoral head along the neck axis and maintain the described configuration.

DETAILED DESCRIPTION OF THE PREFERRED EMBODIMENT

Figure 1:
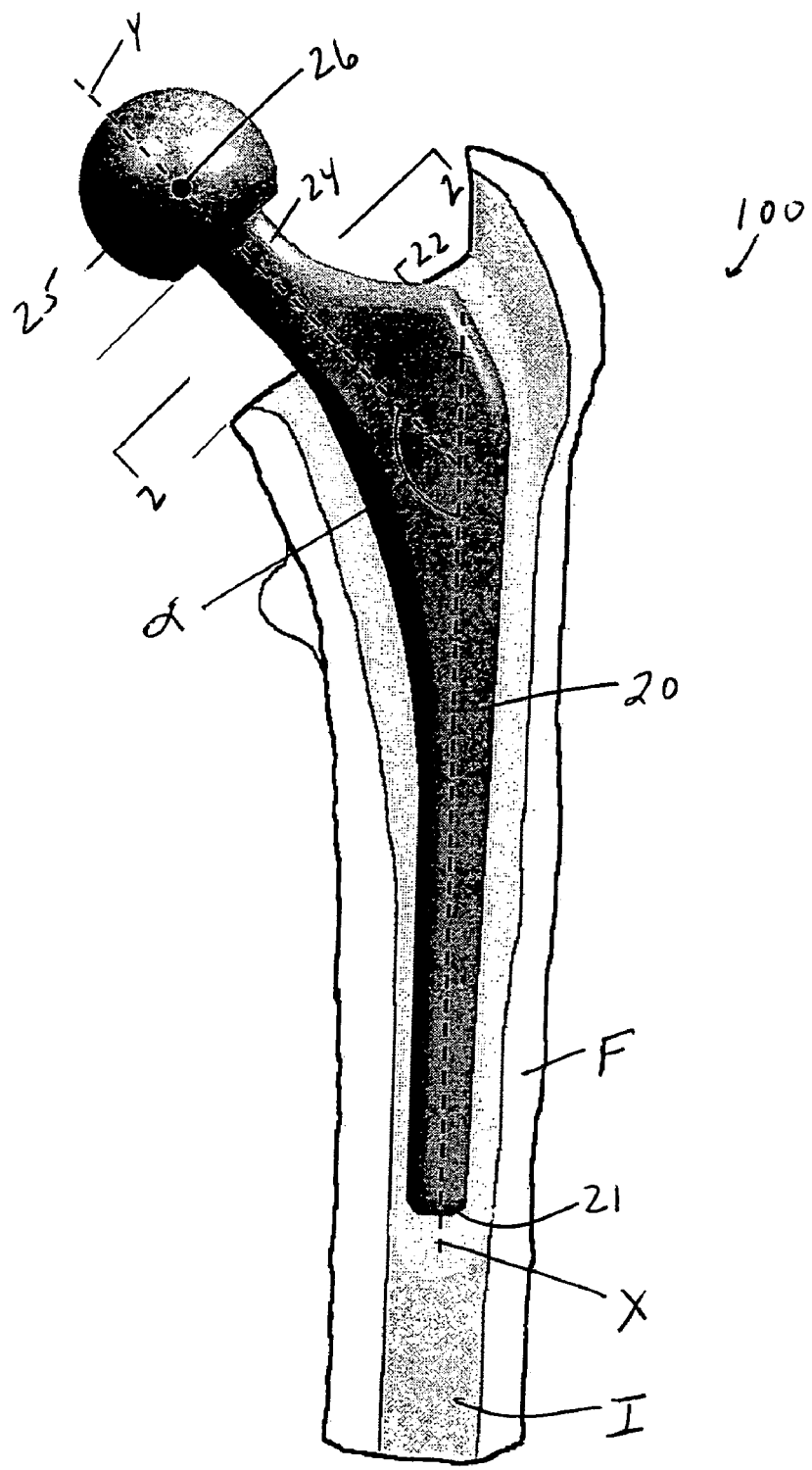
FIG. 1 is a side view of a femoral implant engaged within a femur.

Referring now to FIG. 1, the present invention is directed to a femoral hip prosthetic implant 100 comprising a longitudinal stem 20. FIG. 1 illustrates an anterior view of a left femoral implant (or a posterior view of a right femoral implant). As illustrated, the stem is engaged within a surgically prepared intramedullary shaft I of the femur F. The stem further comprises a distal end 21 and a proximal end 22, with a longitudinal axis X extending from the proximal end to the distal end. Extending from the proximal end of the stem is a neck 24 portion and a femoral head 25 configured for engagement within an acetabulum (not shown). The implant further includes a second longitudinal axis Y extending from and through the femoral head 25 and neck portion 24. The neck axis Y intersects the stem axis X, generally at an angle α, as shown in FIG. 1.

Figure 2:
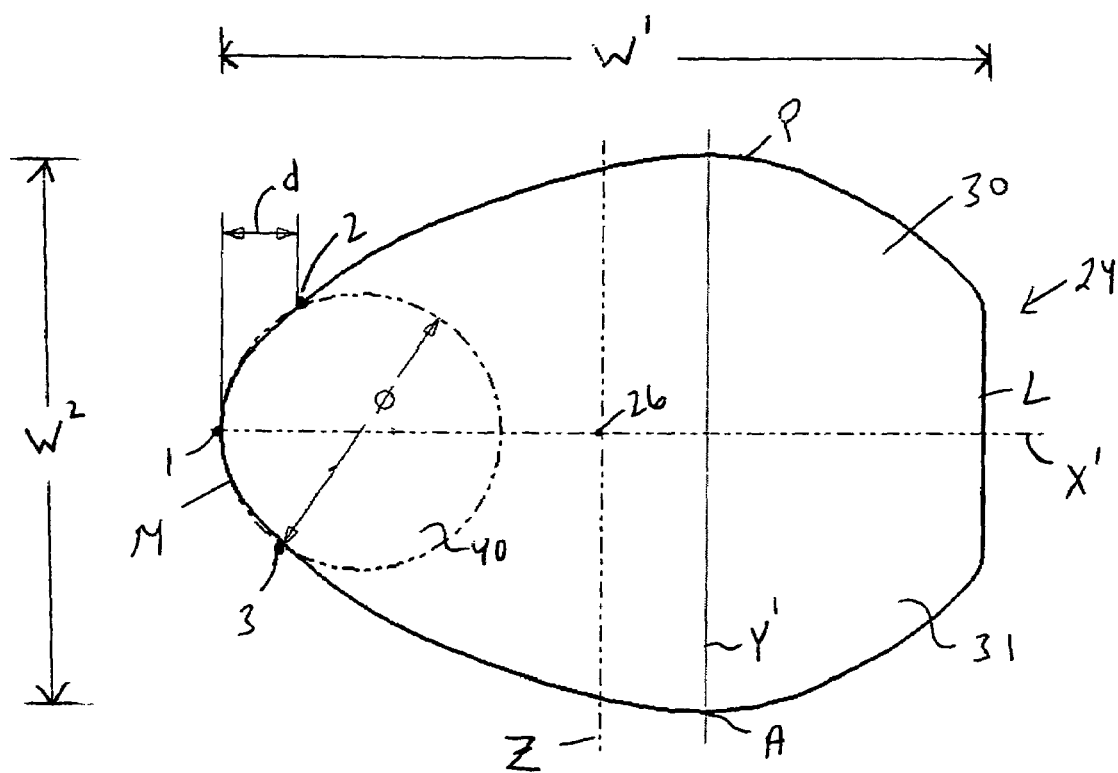
FIG. 2 is a transverse cross-sectional view of the neck portion of the femoral implant, taken along lines 2—2 of FIG. 1.
Figure 3:
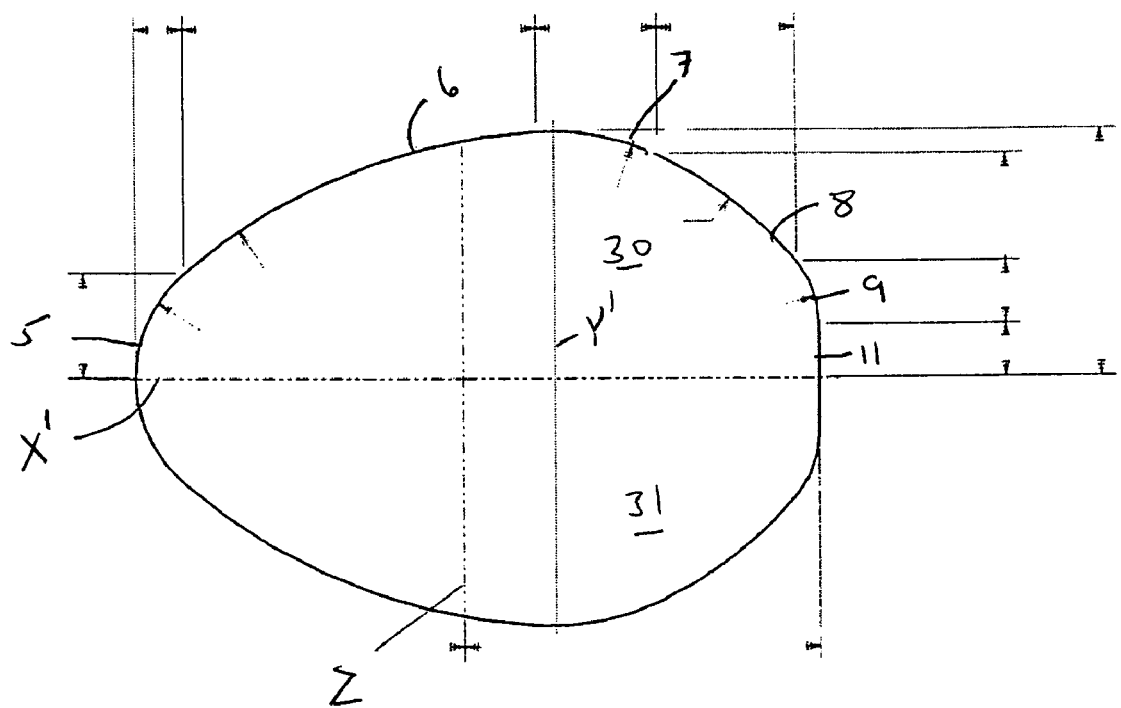
FIG. 3 is a similar transverse cross-sectional view of the neck portion of the femoral implant, taken along lines 2—2 of FIG. 1.
Figure 4:
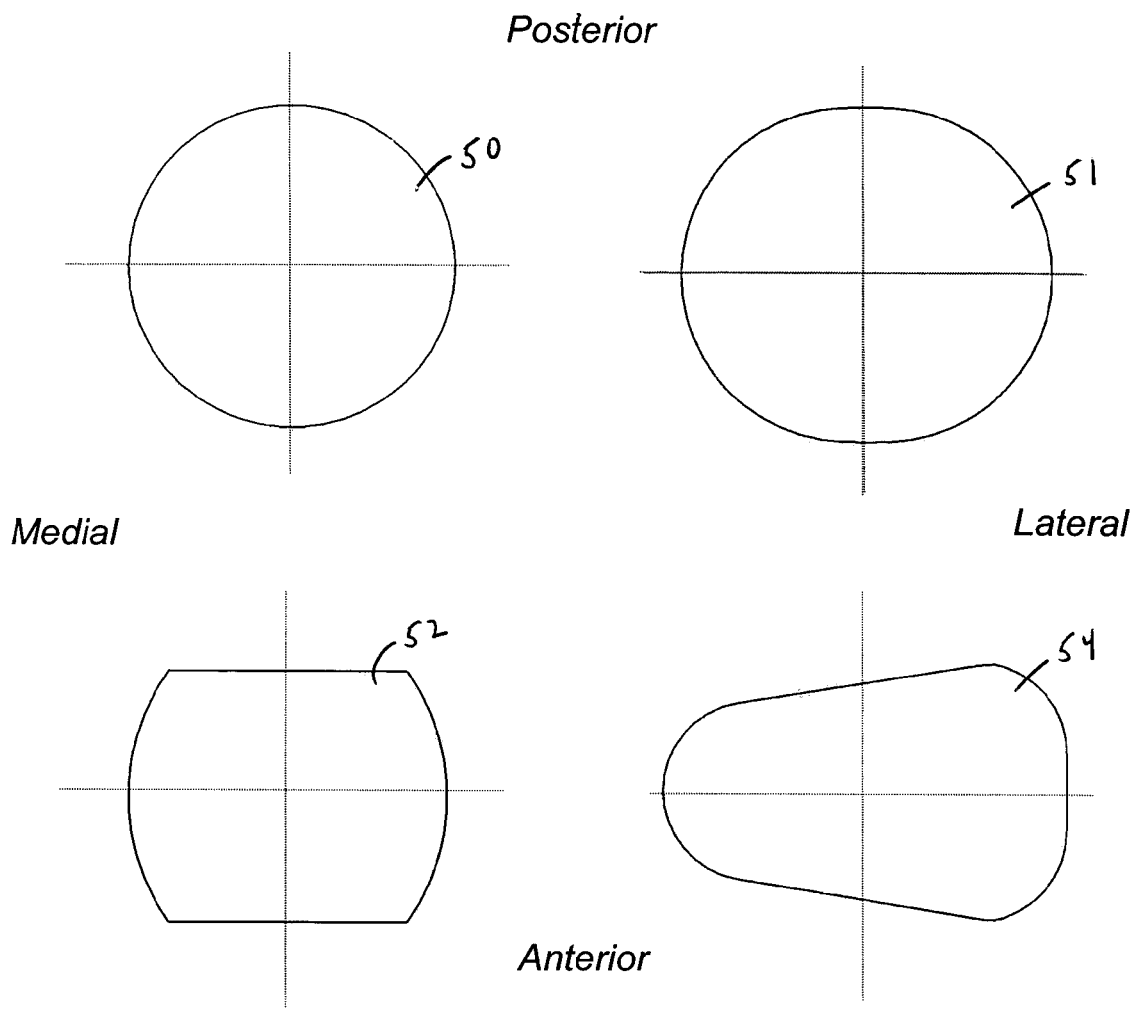
FIG. 4 illustrates transverse cross-sectional views of different neck configurations for current femoral implants.

The novel aspects of the present invention reside within the configuration of the neck portion 24 of the implant and may be best described and illustrated with respect to a transverse cross-section taken perpendicular to the neck axis Y of the implant (i.e. along line 2—2 in FIG. 1), as illustrated in FIG. 2. The novel transverse cross sectional design of the neck portion of the implant is defined in part with respect to two axes $X^1$, $Y^1$ that intersect one another within the same plane of the cross section. Specifically, the cross section comprises a medial/lateral axis $X^1$ bisecting the cross section through a medial-most point 1 along the medial edge M and through the lateral edge L of the cross section. Consequently, two anterior 30 and posterior 31 halves are created about the medial/lateral axis $X^1$. The medial/lateral axis further defines a maximum medial/lateral width $W^1$ of the cross-section. FIGS. 2–3 illustrate one configuration of the anterior 30 and posterior 31 halves; however, the configuration of these halves 30, 31 may be modified. For example, the anterior A and posterior edges P may be slightly flattened, concaved, or more convexed than that shown in the figures. Preferably, from the standpoint of increased versatility of the implant, the anterior 30 and posterior 31 halves are substantially symmetrical such that one implant may be used for both the right and left legs, thereby reducing the inventory demands and subsequent costs associated therewith.

The transverse cross section may also be defined in part by a maximum anterior/posterior axis $Y^1$ that perpendicularly intersects the medial/lateral axis $X^1$ and the anterior A and posterior P edges of the cross section at the widest anterior/posterior points of the cross-section, to thereby define a maximum anterior/posterior width $W^2$ of the cross section. As shown in FIGS. 2–3, the maximum anterior/posterior axis $Y^1$ runs parallel to a second anterior/posterior axis Z, this second axis Z oriented such that it intersects the medial/lateral axis $X^1$ point 26 representing the location of the neck axis Y as it intersects the center 26 of the femoral head 25. The maximum anterior/posterior width $W^2$ as well as the medial lateral width $W^1$ is typically about 8 mm or greater, and more typically from about 9 mm to about 15 mm. A preferred medial lateral width $W^1$ is from about 8 mm to 12 mm.

Figure 6A:
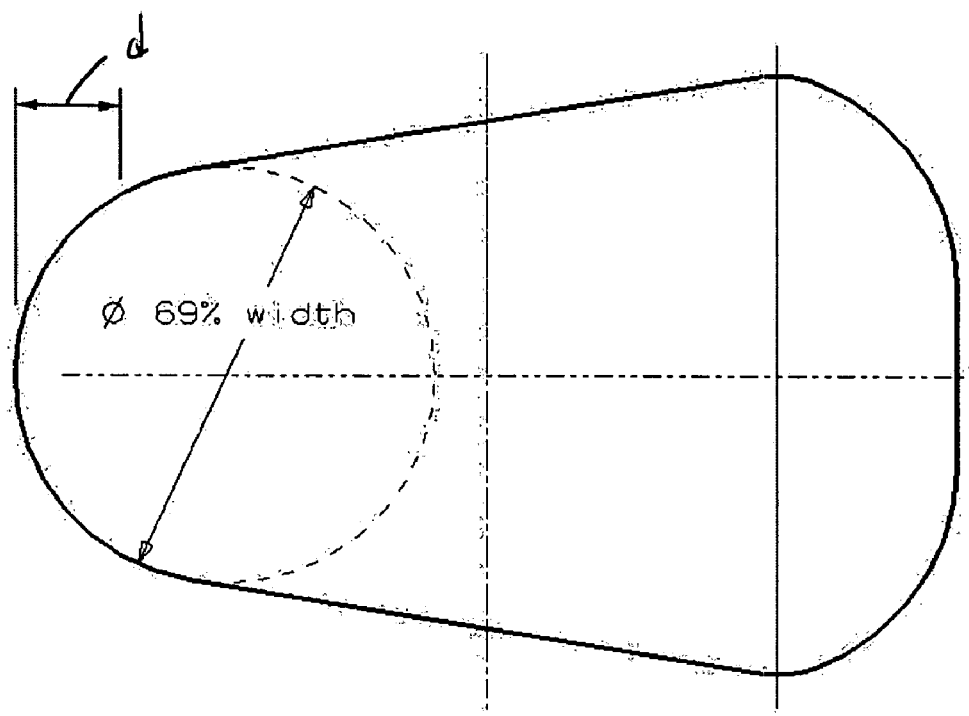
FIGS. 6A–6C illustrate transverse cross-sectional views of conventional neck configurations, further illustrating the medially-positioned circle and relationship between the effective medial diameter of the circle and the maximum anterior/posterior width of each design as a comparison to that of the present invention.
Figure 6B:
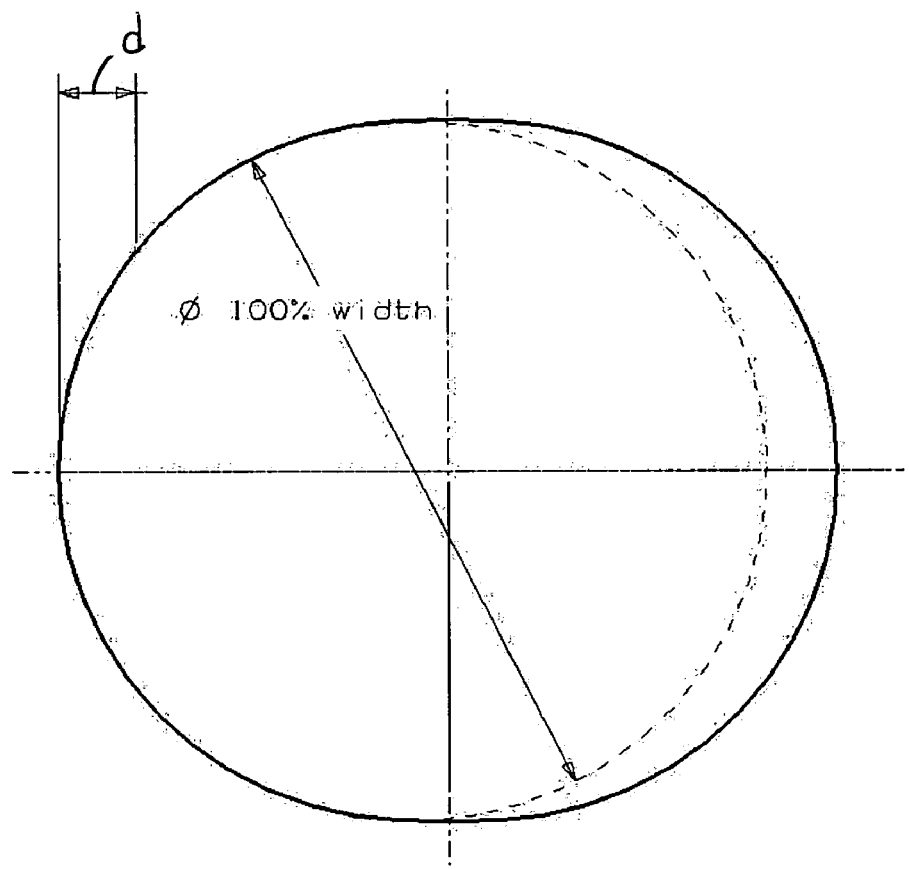
Figure 6C:
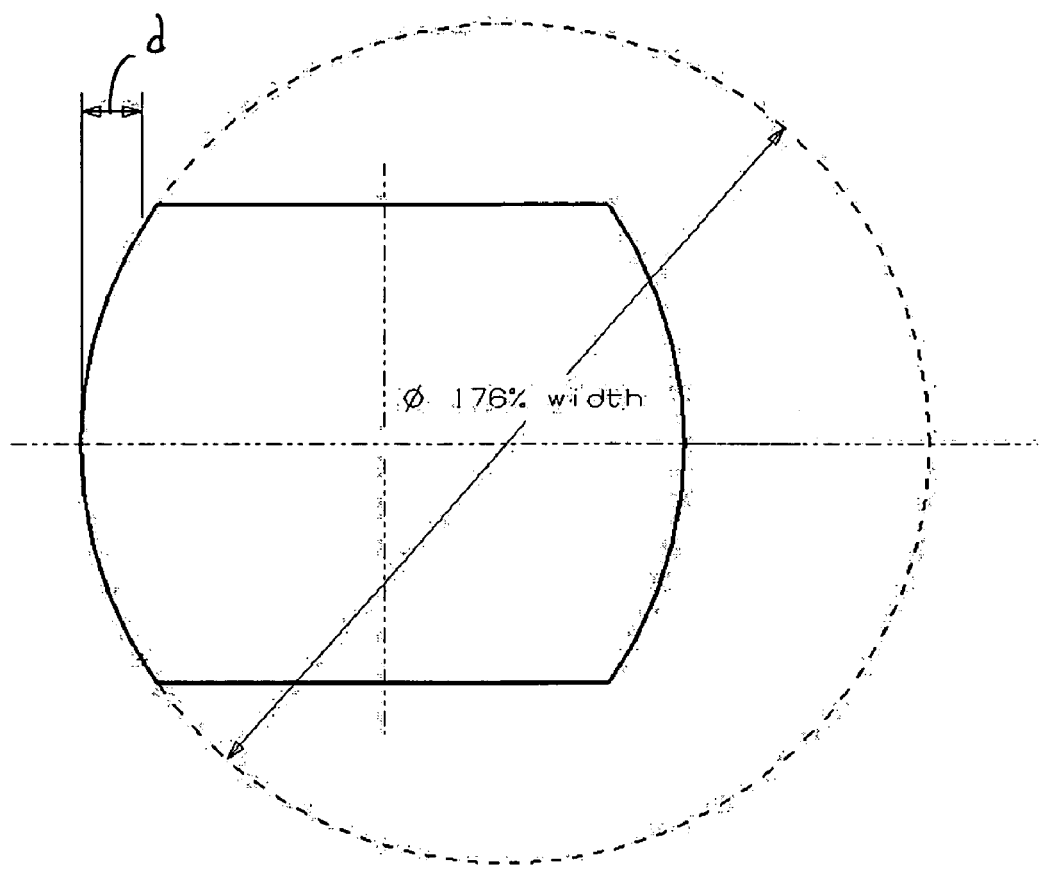

The configuration of the neck portion, with respect to the transverse cross section, is further defined geometrically by a medially-positioned circle 40 comprising three points along its circumference: (1) the medial-most point 1 of the cross section through which the medial/lateral axis $X^1$ intersects; (2) a point 2 taken on the anterior edge A of the cross section; and 3) a point 3 the taken on the posterior edge P of the cross section. The anterior and posterior edge points 2,3 are further located along the anterior and posterior edges, respectively, at a distance d of 10% of the medial/lateral width $W^1$ measured laterally from the medial-most point 1. For example, if the medial/lateral width $W^1$ is 12 mm, the anterior and posterior edge points 2,3 are taken at 1.2 mm measured from the medial-most point 1. Moreover, the effective medial diameter (represented as a double arrow line θ) of the medially-positioned circle 40 is about 66% or less of the anterior/posterior width of the cross section, as defined by the maximum anterior/posterior axis $Y^1$. Thus, if the maximum anterior/posterior width $W^2$ is 12 mm, the effective medial diameter will range from about 0.6 mm to about 7.8 mm. As a comparison, the effective medial diameters θ of a circle taken at the same three points in conventional neck designs (i.e. circle, rectangle, trapezoid, and oval) are illustrated in FIGS. 6A–6C.

In the present invention, the configuration of the transverse cross-section just described is the same at one or more points along the neck portion 24 at or between about 10 mm and 22 mm below, or distal to, the expected center 26 of the femoral head 25, as measured along the neck axis Y. That is, the transverse cross-section may be the same for the entire 10 mm–22 mm length, or lengths within the 10 mm–22 mm range (e.g. 14 mm–18 mm, 12 mm–16 mm, and the like), depending upon where along the neck axis Y the expected impingement might be. In particular, it is desirable that the inventive transverse cross-section be located along the neck of the implant such that the expected point of the impingement would be approximately in the center of the range. Factors such as the size of the femoral head (typically ranging from 28 mm to 42 mm) and the shape and size of the bearing surface of the acetabular cup (which may be offset from the center of the outer surface by 0 mm to 7 mm) will affect where the point of impingement might occur along the neck. Such factors are used by those of ordinary skill in the art to readily calculate the expected point of impingement along the neck axis. For example, it is generally known by the skilled artisan that a femoral implant with a 32 mm head and a perfectly semi-spherical acetabular cup would impinge approximately 16 mm down the neck axis. Consequently, the femoral stem used to accommodate the 32 mm head should have the inventive transverse cross-section located within the range of about 14 mm–18 mm; however, it will be appreciated by those of ordinary skill in the art that this range may be moved slightly along the neck axis distally or proximally if desired. Moreover, while the inventive transverse cross-section may indeed be present over the entire 10 mm–22 mm range of the femoral neck, it will also be recognized that such a design may possibly compromise the strength of the implant, and thus, it may be more preferable that the design be present within a narrower range in order to cover the expected point(s) of impingement, as described above.

Figure 7:
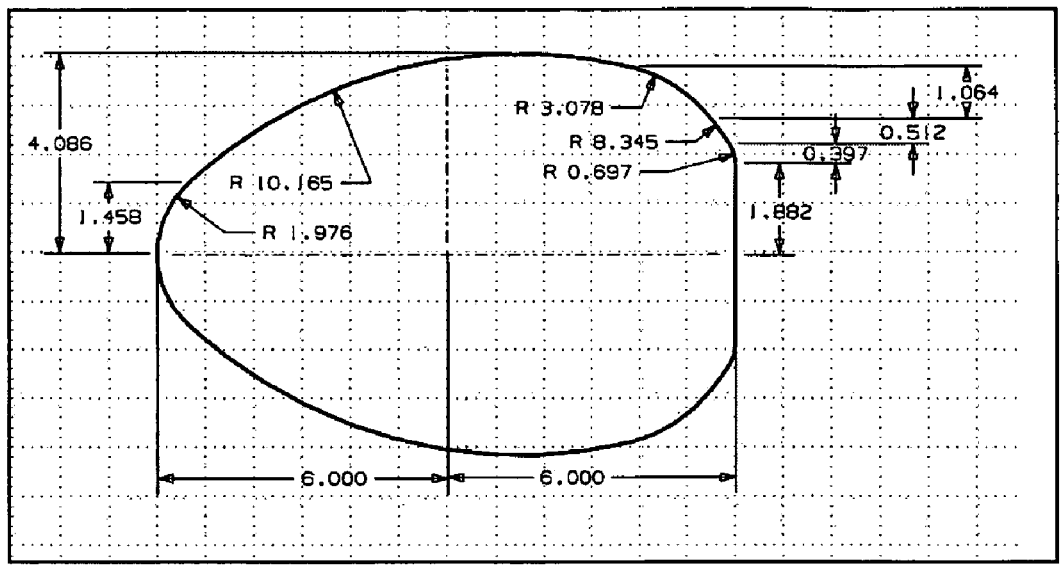
FIG. 7 is the same transverse cross section as illustrated in FIG. 3, including specific dimensions.

In a preferred configuration, as best illustrated in FIGS. 3 and 7 (FIG. 7 contains actual dimensions), the outer edge of the anterior A and posterior P portions of the transverse cross section, as defined by the medial/lateral axis $X^1$, comprises a medial arc 5, a series of five tangent arcs 6–9, and a flat edge 11 on the lateral side L. This embodiment has an advantage in that the edges are smooth and continuous and its shape allows optimal range of motion without jeopardizing strength. However, very similar cross-sections could be formed using less tangential arcs or no lateral flat without significantly altering the range of motion or strength of the neck. One of the primary advantages of the present invention is the small medial width, as defined above and illustrated herein with respect to the medially-positioned circle 40. The embodiment illustrated herein is just one example that benefits from the small medial width of the cross section.

It will be appreciated by those of ordinary skill in the art that the inventive femoral implant may be fabricated using any number of types metals and/or metal alloys commonly used in the manufacture of orthopedic prostheses.

The novel configuration of the neck portion of the inventive femoral implant provides significant advantages over current neck designs (i.e. circular, rectangular, oval, and trapezoid designs). As described in Example 1, the inventive femoral implant matches or increases the range of motion for several bending activities without sacrificing the strength of the neck portion. The invention also increases the range of motion for a broad array of non-bending activities performed in daily living that are known to place the artificial joint at risk of dislocation due to impingement with the acetabulum.

The preferred embodiment of the present invention provides considerable range of motion and adequate neck strength at common neck angles α typically ranging from about 125° to about 140° for a particular femoral stem. Still other advantages of the invention to accommodate various neck-shaft angles, femoral stem designs, and varying femoral component materials will be readily apparent from the general description. As will be recognized by those of ordinary skill in the art, the invention is capable of other and different embodiments and its several details are capable of modifications in various respects, all without departing from the spirit of the invention.

EXAMPLE 1

Figure 5:
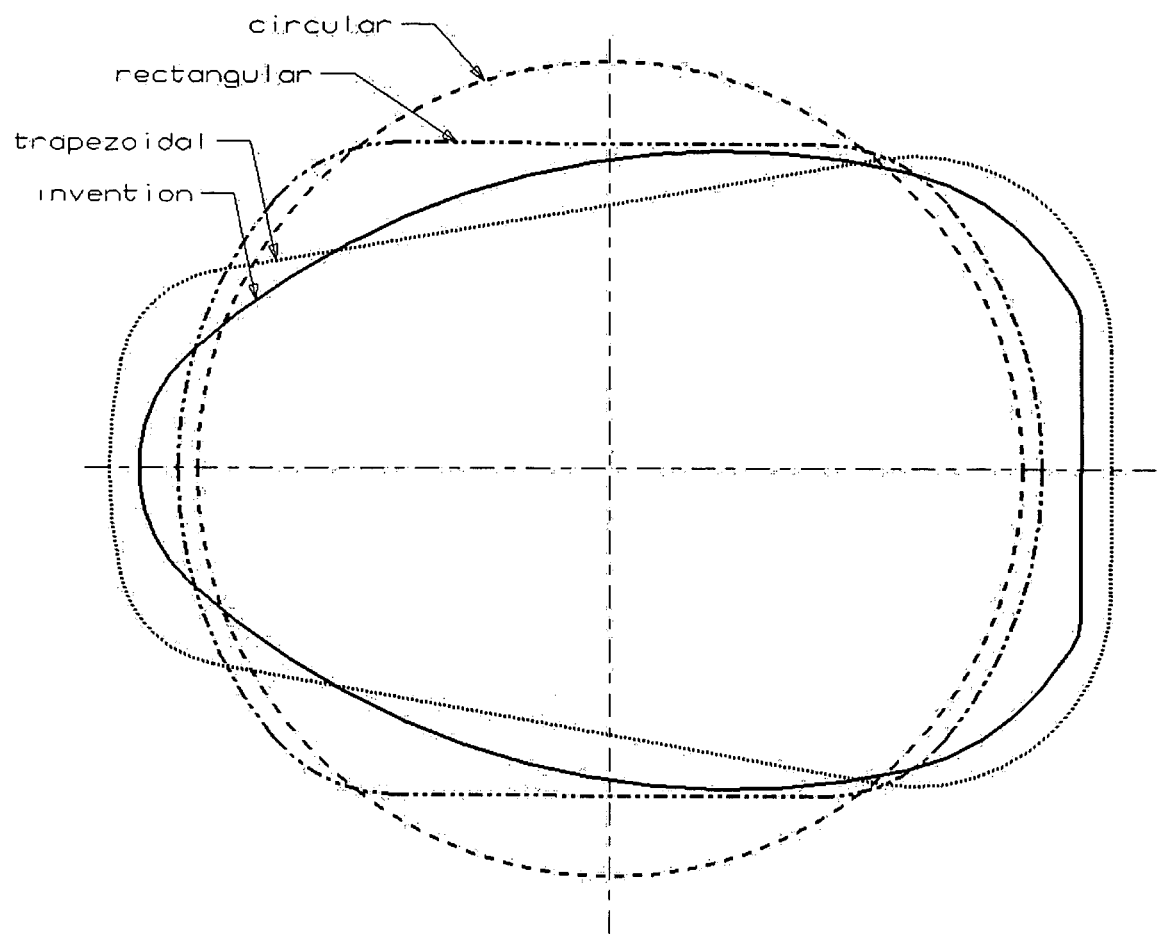
FIG. 5 illustrates an overlay of transverse cross-sectional views of the conventional neck configurations and the neck configuration of the present invention.

To make an accurate assessment of the range of motion provided by the present invention, CAD models were prepared of the preferred embodiment (illustrated in FIG. 7) and of conventional circular, rectangular, and trapezoidal designs. In each model, the cross-sectional geometry of the neck was held constant over a distance of 14 mm to 18 mm from the head center along the neck axis. Below this level, each neck was blended to a larger version of the cross-section, such that, at a level along the neck axis 35 mm below the head center, the medial-lateral and anterior-posterior width of the cross-section increased by 9 mm (FIG. 5).

The neck was placed in 15° of anteversion, 6° of adduction, and 5° of flexion relative to the longitudinal axis of the femur, and a load typically experienced by the femoral component during walking (Bergmann et al., 2001) was applied to the head center using finite element analysis software (Unigraphics NX). The dimensions of all four designs were scaled such that the strength of each design, as represented by the maximum Von Mises stress, matched that of the preferred embodiment under identical loading conditions simulating the loading of the hip during walking. The cross-sections of equalized walking strength can be seen in FIG. 5.

After each cross-section was adjusted for equal strength, the motion of each model to impingement was simulated using CAD models of a standard femoral stem utilizing each of the four different neck designs, each having a 32 mm femoral head. Each model was initially positioned in 15° of anteversion, 6° of adduction, and 5° of flexion relative to the longitudinal axis of the femur. The head of each femoral component was articulated with a 3D solid model of an acetabular cup, placed in 45° of inclination and 20° of anteversion.

Each femoral component was then placed in the orientation associated with activities known to cause impingement and dislocation (Johnston and Smidt 1970, Wyss 2001, Nadzadi et al., 2003). For each activity, a predetermined angle of rotation was applied about two of the three axes of the hip, and the third rotation angle was increased until impingement occurred. The rotations for each activity are outlined in Table 1.

TABLE 1

Activities simulated with the virtual impingement model and the corresponding variation of stem orientation.

| Activity | Flexion (deg) | Adduction (deg) | Internal Rotation (deg) |
|---|---|---|---|
| Pure flexion | flexion to impingement | 0 | 0 |
| Shoe tying | flexion to impingement | 17.5 | 9 |
| rolling | flexion to impingement | 10 | 45 |
| sit to stand | flexion to impingement | 0 | 25 |
| stooping | flexion to impingement | 10 | 25 |
| crossing legs | 98.5 | 16 | external rotation to impingement |

Results of the virtual impingement model show that the invention matched or increased the range of motion over the prior art in all six activities. For sit to stand and stooping, the range of motion was 9° and 5° greater than any of the prior art modeled. Complete results of the range of motion comparison are shown in Table 2.

TABLE 2

Resulting ranges of motion (in degrees) for the prior art and an embodiment of the invention from the virtual impingement model.

| Design | pure flexion | tie (flex) | roll (ext) | Sit-to stand (flex) | stoop (flex) | Leg-cross (ext rot) | Maximum stress (Von Mises, MPa) |
|---|---|---|---|---|---|---|---|
| Circular | 133 | 111 | 24 | 113 | 105 | 91 | 196.3 |
| Rectangular | 132 | 109 | 25 | 112 | 104 | 90 | 196.6 |
| Trapezoidal | 128 | 108 | 23 | 115 | 106 | 94 | 196.0 |
| Invention | 133 | 112 | 25 | 124 | 110 | 97 | 196.0 |

The invention claimed is:

1. A prosthetic femoral implant suitable for use in hip arthroplasty, said implant comprising:
   a. a longitudinal stem having a distal end and a proximal end, said stem further having a longitudinal axis extending from said proximal end to said distal end;
   b. a neck portion extending from said proximal end of said stem and having a femoral head configure for engagement within an acetabulum;
   c. said neck portion having an axis extending through said femoral head and neck portion to intersect said stem axis, and wherein a transverse cross section of said neck portion taken perpendicular to said neck axis further comprises (i) a medial/lateral axis bisecting said cross section through a medial-most point along said medial edge and a point along said lateral edge of said cross section, thereby creating two anterior and posterior halves about said medial/lateral axis, said medial/lateral axis further defining a maximum medial/lateral width of said cross-section; and (ii) a maximum anterior/posterior axis intersecting said anterior and posterior edges and said medial/lateral axis to define a maximum anterior/posterior width of said cross section;
   d. said transverse cross section further having a configuration defined by a medially-positioned circle comprising (i) said medial-most point of said cross section, (ii) a point taken on said anterior edge of said cross section, and (iii) a point taken on said posterior edge of said cross section, wherein each of said anterior and posterior edge points are located along said anterior and posterior edges, respectively, at a distance of 10% of said maximum medial/lateral width measured laterally from said medial-most edge point; and e. said medially-positioned circle having a medial diameter ranging in length of about 66% or less of said maximum anterior/posterior width of said cross section.

2. The implant of claim 1, wherein said transverse cross section is taken at one or more points located at or between about 10 mm to about 22 mm below a center of said femoral head along said neck axis.

3. The implant of claim 1, wherein said medial diameter is about 55% or less of said maximum anterior/posterior width of said cross section.

4. The implant of claim 3, wherein said transverse cross section is taken at one or more points located at or between about 10 mm to about 22 mm below a center of said femoral head along said neck axis.

5. The implant of claim 3, wherein said medial diameter is from about 40% to about 50% of said maximum anterior/posterior width of said cross section.

6. The implant of claim 5, wherein said transverse cross section is taken at one or more points located at or between about 10 mm to about 22 mm below a center of said femoral head along said neck axis.

7. The implant of claim 2, wherein said transverse cross section is taken at one or more points located at or between about 12 mm to about 18 mm below a center of said femoral head along said neck axis.

8. The implant of claim 7, wherein said medial diameter is about 55% or less of said maximum anterior/posterior width of said cross section.

9. The implant of claim 8, wherein said medial diameter is from about 40% to about 50% of said maximum anterior/posterior width of said cross section.

10. A prosthetic femoral implant suitable for use in hip arthroplasty, said implant comprising:
   a. a longitudinal stem having a distal end and a proximal end, said stem further having a longitudinal axis extending from said proximal end to said distal end;
   b. a neck portion extending from said proximal end of said stem and having a femoral head configured for engagement within an acetabulum;
   c. said neck portion having an axis extending through said femoral head and neck portion to intersect said stem axis, and wherein a transverse cross section of said neck portion taken perpendicular to said neck axis further comprises (i) a medial/lateral axis bisecting said cross section through a medial-most point along said medial edge and a point along said lateral edge of said cross section, thereby creating two anterior and posterior halves about said medial/lateral axis, said medial/lateral axis further defining a maximum medial/lateral width of about 9 mm or greater; and (ii) a maximum anterior/posterior axis intersecting said anterior and posterior edges and said medial/lateral axis to define a maximum anterior/posterior width of said cross-section;
   d. said transverse cross section further having a configuration defined by a medially-positioned circle comprising (i) said medial-most point of said cross section, (ii) a point taken on said anterior edge of said cross section, and (iii) a point taken on said posterior edge of said cross section, wherein each of said anterior and posterior edge points are located along said anterior and posterior edges, respectively, at a distance of 10% of said medial/lateral width measured laterally from said medial-most edge point; and
   e. said medially-positioned circle having a medial diameter ranging in length of about 66% or less of said maximum anterior/posterior width of said cross section.

11. The implant of claim 10, wherein said transverse cross section is taken at one or more points located at or between about 10 mm to about 22 mm below a center of said femoral head along said neck axis.

12. The implant of claim 10, wherein said medial diameter is about 55% or less of said maximum anterior/posterior width of said cross section.

13. The implant of claim 12, wherein said transverse cross section is taken at one or more points located at or between about 10 mm to about 22 mm below a center of said femoral head along said neck axis.

14. The implant of claim 12, wherein said medial diameter is from about 40% to about 50% of said maximum anterior/posterior width of said cross section.

15. The implant of claim 14, wherein said transverse cross section is taken at one or more points located at or between about 10 mm to about 22 mm below a center of said femoral head along said neck axis.

16. The implant of claim 10, wherein said maximum medial/lateral width is about 10 mm or greater.

17. The implant of claim 16, wherein said transverse cross section is taken at one or more points located at or between about 10 mm to about 22 mm below a center of said femoral head along said neck axis.

18. The implant of claim 17, wherein said medial diameter is about 55% or less of said maximum anterior/posterior width of said cross section.

19. The implant of claim 18, wherein said transverse cross section is taken at one or more points located at or between about 10 mm to about 22 mm below a center of said femoral head along said neck axis.

20. The implant of claim 18, wherein said medial diameter is from about 40% to about 50% of said maximum anterior/posterior width of said cross section.

21. A prosthetic femoral implant suitable for use in hip arthroplasty, said implant comprising:
   a. a longitudinal stem having a distal end and a proximal end, said stem further having a longitudinal axis extending from said proximal end to said distal end;
   b. a neck portion extending from said proximal end of said stem and having a femoral head configured for engagement within an acetabulum;
   c. said neck portion having an axis extending through said femoral head and neck portion to intersect said stem axis, and wherein a transverse cross section of said neck portion taken perpendicular to said neck axis further comprises (i) a medial/lateral axis bisecting said cross section through a medial-most point along said medial edge and a point along said lateral edge of said cross section, thereby creating two substantially symmetrical anterior and posterior halves about said medial/lateral axis, said medial/lateral axis further defining a maximum medial/lateral width of said cross-section; and (ii) a maximum anterior/posterior axis intersecting said anterior and posterior edges and said medial/lateral axis to define a maximum anterior/posterior width of said cross section;
   d. said transverse cross section further having a configuration defined by a medially-positioned circle comprising (i) said medial-most point of said cross section, (ii) a point taken on said anterior edge of said cross section, and (iii) a point taken on said posterior edge of said cross section, wherein each of said anterior and posterior edge points are located along said anterior and posterior edges, respectively, at a distance of 10% of said maximum medial/lateral width measured laterally from said medial-most edge point; and e. said medially-positioned circle having a medial diameter ranging in length of about 66% or less of said maximum anterior/posterior width of said cross section.

22. The implant of claim 21, wherein said transverse cross section is taken at one or more points located at or between about 10 mm to about 22 mm below a center of said femoral head along said neck axis.

23. The implant of claim 21, wherein said medial diameter is about 55% or less of said maximum anterior/posterior width of said cross section.

24. The implant of claim 23, wherein said transverse cross section is taken at one or more points located at or between about 10 mm to about 22 mm below a center of said femoral head along said neck axis.

25. The implant of claim 23, wherein said medial diameter is from about 40% to about 50% of said maximum anterior/posterior width of said cross section.

26. The implant of claim 25, wherein said transverse cross section is taken at one or more points located at or between about 10 mm to about 22 mm below a center of said femoral head along said neck axis.

27. The implant of claim 22, wherein said transverse cross section is taken at one or more points located at or between about 12 mm to about 18 mm below a center of said femoral head along said neck axis.

28. The implant of claim 27, wherein said medial diameter is about 55% or less of said maximum anterior/posterior width of said cross section.

29. The implant of claim 28, wherein said medial diameter is from about 40% to about 50% of said maximum anterior/posterior width of said cross section.

30. The implant of claim 21, wherein said maximum medial/lateral width is about 9 mm or greater.

31. The implant of claim 30, wherein said transverse cross section is taken at one or more points located at or between about 10 mm to about 22 mm below a center of said femoral head along said neck axis.

32. The implant of claim 30, wherein said medial diameter is about 55% or less of said maximum anterior/posterior width of said cross section.

33. The implant of claim 32, wherein said transverse cross section is taken at one or more points located at or between about 10 mm to about 22 mm below a center of said femoral head along said neck axis.

34. The implant of claim 33, wherein said medial diameter is from about 40% to about 50% of said maximum anterior/posterior width of said cross section.

35. The implant of claim 21, wherein said maximum medial/lateral width is about 10 mm or greater.

36. The implant of claim 35, wherein said transverse cross section is taken at one or more point located at or between about 10 mm to about 22 mm below a center of said femoral head along said neck axis.

37. The implant of claim 35, wherein said medial diameter is about 55% or less of said maximum anterior/posterior width of said cross section.

38. The implant of claim 37, wherein said transverse cross section is taken at one or more points located at or between about 10 mm to about 22 mm below a center of said femoral head along said neck axis.

39. The implant of claim 38, wherein said medial diameter is from about 40% to about 50% of said maximum anterior/posterior width of said cross section.

40. The implant of claim 31, wherein said transverse cross section is taken at one or more points located at or between about 12 mm to about 18 mm below a center of said femoral head along said neck axis.

41. The implant of claim 40, wherein said medial diameter is about 55% or less of said maximum anterior/posterior width of said cross section.

42. The implant of claim 41, wherein said medial diameter is from about 40% to about 50% of said maximum anterior/posterior width of said cross section.

* * * * *

UNITED STATES PATENT AND TRADEMARK OFFICE
CERTIFICATE OF CORRECTION

| | | |
|---|---|---|
| PATENT NO. | : 7,060,102 B2 | Page 1 of 1 |
| APPLICATION NO. | : 10/762213 | |
| DATED | : June 13, 2006 | |
| INVENTOR(S) | : Matthew T. Thompson and James D. Johnston | |

It is certified that error appears in the above-identified patent and that said Letters Patent is hereby corrected as shown below:

On page 1, under "Inventors", replace "Johnson" with -- Johnston --

Signed and Sealed this

Thirtieth Day of January, 2007

JON W. DUDAS
*Director of the United States Patent and Trademark Office*